United States Patent [19]

Röhlk

[11] Patent Number: 5,273,627
[45] Date of Patent: Dec. 28, 1993

[54] PROCESS FOR STRIPPING AND DISTILLING MIXTURES CONTAINING ALKYLAROMATICS CHLORINATED IN THE SIDE CHAIN

[75] Inventor: Kai Röhlk, Bergisch Gladbach, Fed. Rep. of Germany

[73] Assignee: Bayer Aktiengesellschaft, Leverkusen, Fed. Rep. of Germany

[21] Appl. No.: 649,269

[22] Filed: Jan. 30, 1991

Related U.S. Application Data

[63] Continuation of Ser. No. 430,205, Nov. 1, 1989, abandoned.

[30] Foreign Application Priority Data

Nov. 24, 1988 [DE] Fed. Rep. of Germany ....... 3839571

[51] Int. Cl.5 .......................... B01D 3/00; C07C 17/38
[52] U.S. Cl. ......................................... 203/38; 203/49; 203/71; 570/211
[58] Field of Search ................... 203/6, 38, 49, 59, 71; 570/211, 207

[56] References Cited

U.S. PATENT DOCUMENTS

| 1,804,458 | 5/1929 | Britton | 570/211 |
| 2,025,024 | 12/1935 | Britton . | |
| 2,543,575 | 2/1951 | Harvey . | |
| 2,564,506 | 8/1951 | Schaeffer | 570/211 |
| 2,564,507 | 8/1951 | Schaeffer | 570/211 |
| 3,715,283 | 2/1973 | Bockmann | 570/211 |
| 3,919,054 | 11/1975 | Hands et al. . | |

FOREIGN PATENT DOCUMENTS

| 0334025 | 9/1989 | European Pat. Off. . | |
| 2543992 | 4/1977 | Fed. Rep. of Germany . | |
| 121776 | 1/1976 | German Democratic Rep. . | |
| 53-31628 | 3/1978 | Japan | 570/211 |
| 644768 | 1/1979 | U.S.S.R. | 570/211 |
| 772080 | 12/1981 | U.S.S.R. | 570/211 |
| 1410474 | 10/1975 | United Kingdom | 570/211 |

*Primary Examiner*—Wilbur Bascomb, Jr.
*Attorney, Agent, or Firm*—Sprung, Horn, Kramer & Woods

[57] ABSTRACT

Mixtures containing alkylaromatrics chlorinated in the side chain are worked up by blowing them out with an inert gas before distillation at elevated temperature and carrying out the distillation in the presence of amines and/or chlorinated amines.

11 Claims, No Drawings

PROCESS FOR STRIPPING AND DISTILLING MIXTURES CONTAINING ALKYLAROMATICS CHLORINATED IN THE SIDE CHAIN

This application is a continuation of application Ser. No. 430,205, filed Nov. 1, 1989, abandoned.

The present invention relates to an improved distillative working up of mixtures containing alkylaromatris chlorinated in the side chain. In the working up according to the invention, side reactions during the distillation are largely eliminated by specific measures.

Alkylaromatics chlorinated in the side chain, for example benzyl chlorides, benzal chlorides and benzotrichlorides, and hydrolysis products thereof, for example benzyl alcohols, benzaldehydes, benzoic acids and benzoyl chlorides, are important intermediate products which are produced in large amounts and are used, for example, for the preparation of plant protection agents, pharmaceuticals, dyestuffs and perfumes (see Kirk-Othmer, Encyclopedia of Chemical Technology, 2nd Ed., Volume 5, pages 281-289 (1964)).

Alkylaromatics chlorinated in the side chain are usually prepared by side chain chlorination of the corresponding alkylaromatics. This reaction is carried out at elevated temperature and if appropriate under irradiation, individual alkylaromatics chlorinated in the side chain always being obtained with only a low selectivity and having to be separated off from other alkylaromatics chlorinated in the side chain and/or starting substances and/or by-products. The reaction mixtures present after the chlorination always contain several components. For example, if o-chlorotoluene is chlorinated in this manner, the chlorination can be carried out, for example, up to the following stages:

Stage I: Until no noticeable amounts of o-chlorobenzal chloride are yet formed. The chlorination product then essentially contains unreacted o-chlorotoluene and o-chlorobenzyl chloride.

Stage II: Until the maximum amount of o-chlorobenzyl chloride has formed. The chlorination product then essentially contains o-chlorobenzyl chloride, a little unreacted o-chlorotoluene and a little o-chlorobenzal chloride.

Stage III: Until no noticeable amounts of o-chlorobenzotrichloride are yet formed. The chlorination product then essentially contains o-chlorobenzyl chloride, benzal chloride and a little unreacted o-chlorotoluene.

Stage IV: Until practically all the o-chlorotoluene has reacted. The chlorination product then essentially contains o-chlorobenzyl chloride, o-chlorobenzal chloride and a little o-chlorobenzotrichloride.

Stage V: Until the maximum amount of o-chlorobenzal chloride has formed. The chlorination product then essentially contains o-chlorobenzal chloride, a little o-chlorobenzyl chloride and o-chlorobenzotrichloride.

Stage VI: Until practically no further o-chlorobenzyl chloride is present. The chlorination product then essentially contains o-chlorobenzal chloride and o-chlorobenzotrichloride.

Stage VII: Until practically no by-products caused by hyperchlorination and/or chlorinating cleavage are yet formed. The chlorination product then essentially contains o-chlorobenzotrichloride and little o-chlorobenzal chloride.

Stage VIII: Until practically no further o-chlorobenzal chloride is present. The chlorination product then essentially contains o-chlorobenzotrichloride and by-products formed by hyperchlorination and/or chlorinating cleavage.

In order to obtain pure o-chlorobenzyl chloride, pure o-chlorobenzal chloride and/or pure o-chlorobenzotrichloride, as is necessary for further processing, distillation thus has to be carried out in each case after the chlorination.

Corresponding chlorination product mixtures also arise on chlorination of alkylaromatics other than o-chlorotoluene, and these likewise have to be worked up by distillation in order to obtain products which can be further used.

Under the conditions for such distillative working up (high temperatures, columns with many trays, high reflux ratios; these have to be used because of the high boiling points and the low differences in boiling points of the substances to be separated), side reactions take place to a considerable degree in the distillation columns and secondary units. The secondary units can be, for example, condensers, vaporizers, pipelines, distributors, margin deflectors, sampling points, measuring instruments, packed columns an packings (for example of ceramic material). The side reactions can be, for example, condensation reactions between 2 and/or more molecules of alkylaromatics chlorinated in the side chain, spontaneous decompositions, polymerizations and corrosion. These leads not only to losses in products and apparatus materials, but, even more serious, also to deposits in the distillation columns and/or secondary units and therefore to constrictions and blockages in this equipment. Distillation installations for working up mixtures containing alkylaromatics chlorinated in the side chain can therefore often be operated for only a short time, and they then have to be stopped and dismantled and the deposits formed removed. This is very labour- and cost-intensive and does not permit a uniform operating procedure.

Attempts to overcome these problems by using columns with specific packings and/or using specific material (for example enamel, special metals, ceramic, glass or fluorine-containing polymers) have not been satisfactory. Thus, for example, enamel tends to scale off under the temperature conditions present, special metals (such as tantalum) are disproportionately expensive, measuring instruments are frequently not available in such materials, and even ceramic packings are not completely inert.

An improved process has now been found for distillative working up of mixtures containing alkylaromatics chlorinated in the side chain, which is characterized in that the mixture to be distilled is blown out with an inert gas at elevated temperature for the distillation and the distillation is carried out in the presence of amines and/or chlorinated amines.

Mixtures which can be employed in the process according to the invention and contain alkylaromatics chlorinated in the side chain can be of various types. For example, they can contain alkylaromatics of the formula (I)

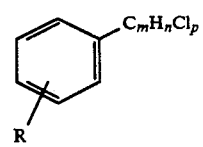

in which
m represents an integer from 1 to 4,
n represents zero or an integer from 1 to 2 m and
p represents an integer form 1 to 2 m+1,
wherein
n+p always gives 2 m+1, and
R denotes 1 to 3 halogen atoms, alkyl or nitro.

If R represents 1 to 3 halogen atoms, these can be, for example, fluorine, chlorine and/or bromine atoms. If R represents alkyl, this can be, for example, $C_1$- to $C_4$-alkyl. Preferably, R denotes 1 to 2 chlorine atoms, methyl, ethyl or nitro.

Mixtures which can be employed can contain one or more compounds of the formula (I). Mixtures which can be employed can furthermore additionally contain, for example, compounds of the formula (II)

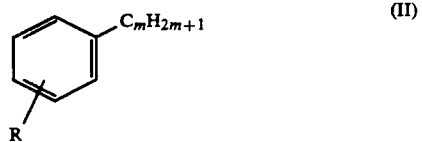

in which m and R have the meaning given in the case of formula (I), and/or compounds which have originated from compounds of the formulae (I) and/or (II) by condensation and/or decomposition.

Mixtures such as are obtained in the side chain chlorination of a compound of the formula (II), it being possible for the chlorination to have been carried out as far as desired, are preferably employed in the process according to the invention. The chlorination can have been carried out, for example, to one of the stages 1 to VIII described above in the case of chlorination of o-chlorotoluene, or in the case of a different starting material up to a corresponding stage. The chlorination here can have been carried out with any desired chlorinating agent. A preferred chlorinating agent is elemental chlorine.

Mixtures containing both alkylaromatics of he formula (I) in which R represents 1 or 2 chlorine atoms and m represents 1 are particularly preferred.

Mixtures which are obtained in the side chain chlorination of chlorotoluenes are especially preferred.

Mixtures which can be employed in the process according to the invention can contain any desired amount of alkylaromatics chlorinated in the side chain. For example, the sum of all the alkylaromatics chlorinated in the side chain which are present in these mixtures can be 15 to 100% by weight. These mixtures preferably contain 20 to 99% by weight of one or more alkylaromatics chlorinated in the side chain.

The blowing out with an inert gas is carried out at elevated temperature. Suitable temperatures are, for example, those int he range from 100° to 200° C. The blowing out is preferably carried out at a temperature of 120° to 180° C. A possible inert gas is, above all, anhydrous nitrogen, but noble gases or mixtures of nitrogen with noble gases are also suitable. Since steam and oxygen are not to be regarded as inert under the conditions to be applied, the inert gas to be employed should be as free as possible form steam and oxygen.

If mixtures from the side chain chlorination of alkylaromatics are employed in the process according to the invention, it is advantageous to carry out the blowing out with an inert gas after the chlorination. In this manner, no expenditure is necessary in order to establish the temperatures suitable for the blowing out, since the side chain chlorination of alkylaromatics is usually carried out at temperatures which are also suitable for the blowing out with an inert gas to be carried out according to the invention.

The blowing out operation can be carried out continuously or discontinuously, and, for example, until the mixture subsequently to be distilled has a content of non-bonded chlorine of less than 10 ppm an contents of hydrogen chloride and water of in each case less than 30 ppm. This is in general the case if 1 to 5 times the volume of inert gas, based on the feed mixture containing the alkylaromatic chlorinated in the side chain, is used for the blowing out.

The amines and/or chlorinated amines are preferably present in all parts of the distillation. In the case of continuous distillation of the mixture containing alkylaromatics chlorinated in the side chain, for example, a procedure can therefore be followed in which amines and/or chlorinated amines having different boiling points are added, and in particular in which at least one amine and/or chlorinated amine is discharged via the top and at least one amine and/or chlorinated amine is discharged via the bottom of the particular distillation column. The amines and/or chloroamines can be added together or separately at any desired point of a continuously operated distillation column, for example close to the addition of or together with the mixture containing alkylaromatics chlorinated in the side chain.

In the case of discontinuous distillation, for example, a procedure can be followed in which a relatively low boiling amine and/or chlorinated amine is continuously added into the retort and is discharged via the top.

Other addition points and forms of addition are of course also possible.

Amines and/or chlorinated amines can be present, for example, in a total amount of 0.02 to 0.2% by weight, based on the mixture to be distilled. Since top products formed in the distillation are often recycled into the chlorination in order finally to prepare more highly chlorinated products, and top products obtained according to the invention contain amines and/or chlorinated amines, it is not always necessary to meter amines and/or chlorinated amines in from the outside. An amine circulation and/or a circulation of chlorinated amines in which top-ups only have to take place from time to time can often be maintained in the manner described in the shorter or longer term.

Examples of amines and/or chlorinated amines are aliphatic and aromatic types, it being possible to employ individual compounds or mixtures. Nitrogen-containing heterocyclics and/or nuclear-chlorinated derivatives thereof are preferred. Pyridine, quinoline and nuclear-chlorinated derivatives of these containing 1 to 3 chlorine atoms, and mixtures of such compounds, are particularly preferred.

The distillative working up of mixtures containing alkylaromatics chlorinated in the side chain can otherwise be carried out in a customary manner, for example in respect of equipment, equipment materials, dimensions, reflux ratios, temperatures, pressures, residence times and the like. The reflux ratios can be, for example, in the range from 1 to 40, preferably in the range from 1 to 8, the temperatures can be, for example, between 100° and 250° C., preferably between 100° and 200° C., the pressure can be, for example, between 1 and 500 mbar, preferably between 30 and 150 mbar, and the residence time can be, for a continuous procedure, for example, between 10 and 120 minutes, preferably between 20 and 40 minutes, and for a discontinuous procedure, for example, between 1 and 100 hours, preferably between 2 and 10 hours.

The process according to the invention leads to drastic reductions in corrosion and side reactions during distillation of mixtures containing alkylaromatics chlorinated in the side chains. Such distillations can thus be carried out in the manner according to the invention without trouble for long periods. It is thus possible to isolate from the mixtures employed higher contents of individual alkylaromatics chlorinated in the side chain and/or individual alkylaromatics chlorinated in the side chain in a higher purity, since a higher distillation expenditure (for example higher columns and multiple distillations) is not associated with a higher risk of blockages and product contamination.

significantly less stable to heat. Exothermic decompositions already occur from about 70° C. in the case of addition of rust, already occur from 35° to 80° C. in the case of addition of iron(III) chloride and already occur from 160° to 180° C. in the case of addition of elemental iron. In addition, if an amine (in this case pyridine) is added in accordance with the present invention, the stability to heat increases to about 250° to 300° C. in samples containing rust and iron(III) chloride and to about 230° to 250° C. in the samples containing elemental iron.

TABLE 1

| | | Temperature ranges of exothermic decomposition reactions with addition of | | | | | |
|---|---|---|---|---|---|---|---|
| | Alkyl-aromatic chlorinated in the side chain | without additive | 0.1% by weight of rust | 0.1% by weight of rust and 0.1% by weight of pyridine | 0.16% by weight of FeCl₃ | 0.09% by weight of FeCl₃ and 0.1% by weight of pyridine | 0.1% by weight of elemental iron | 0.1% by weight of elemental iron and 0.1% weight of pyridine |
| a) | o-chlorobenzyl chloride | over 300° C. | 80–160° C. | over 300° C. | 80–165° C. | over 300° C. | 170–190° C. | over 230° C. |
| b) | o-chlorobenzal chloride | over 300° C. | 85–145° C. | over 300° C. | below 200° C. | over 300° C. | 120–215° C. | over 230° C. |
| c) | o-chlorobenzotrichloride | over 300° C. | 175–280° C. | over 280° C. | 25° C. | over 300° C. | 160–270° C. | over 250° C. |
| d) | 2,4-dichlorobenzyl chloride | over 250° C. | 90–120° C. | over 290° C. | 35–60° C. | over 280° C. | 160–250° C. | over 260° C. |
| e) | 2,4-dichlorobenzal chloride | over 330° C. | from 70° C. | over 250° C. | 80–200° C. | over 260° C. | from 180° C. | over 250° C. |

EXAMPLE 1

Various alkylaromatics chlorinated in the side chain and with and without additives were investigated in respect of their thermal decomposition behaviour by means of differential thermoanalysis (apparatus Mettler TA 2000, general measurement with continuous increasing of the temperature by 5K per minute). The results are summarized in detail in Table 1, in which in each case the temperature range in which exothermic decomposition reactions were observed is stated.

It can be seen that in the pure form ("without additive"), alkylaromatics chlorinated in the side chain are stable to heat up to at least 250° C. After additions of small amounts of rust, iron(III) chloride or elemental iron, which simulate conditions prevailing during handling of such substances in apparatuses made of metal, the alkylaromatics chlorinated in the side chain are

EXAMPLES 2 TO 8 o-Chlorobenzyl chloride without additives, with addition of iron(III) chloride and with additions of iron(III) chloride and various amines and chloroamines was investigated in respect of the thermal decomposition behaviour by means of differential thermal analysis in a manner corresponding to that in Example 1. The results are summarized in detail in Table 2, in which the temperature at which an exothermic decomposition reaction started is given in each case.

It can be seen that pure o-chlorobenzyl chloride is stable up to 300° C. After addition of iron(III) chloride, which simulates the conditions prevailing when handling o-chlorobenzyl chloride in apparatuses made of metal, o-chlorobenzyl chloride is far less stable to heat, since in this case decomposition reactions already start at 95° C. If amines or chloroamines are added in accordance with the present invention (see Examples 4 to 8), the stability to heat rises significantly, Decomposition reactions than only start at temperatures of 135° to 280° C.

TABLE 2

| Example No. | Substance investigated | Start of thermal decomposition reactions |
|---|---|---|
| 2 | o-Chlorobenzyl chloride without additives | 300° C. |
| 3 | o-Chlorobenzyl chloride + 200 ppm of FeCl₃ | 95° C. |
| 4 | o-Chlorobenzyl chloride + 200 ppm of FeCl₃ + 1000 ppm of pyridine | 250° C. |
| 5 | o-Chlorobenzyl chloride + 200 ppm of FeCl₃ + 1000 ppm of 2,6-dichloropyrimidine | 135° C. |
| 6 | o-Chlorobenzyl chloride + 200 ppm of FeCl₃ + 1000 ppm of 2,3,5-trichloropyrimidine | 140° C. |
| 7 | o-Chlorobenzyl chloride + 200 ppm of FeCl₃ + 1000 ppm of 3-chloropyrimidine | 280° C. |
| 8 | o-Chlorobenzyl chloride + 200 ppm of FeCl₃ + 1000 ppm of quinoline | 190° C. |

EXAMPLE 9

A mixture containing 0.5% by weight of o-chlorotoluene, 57.0% by weight of o-chlorobenzyl chloride, 42.0% by weight of o-chlorobenzal chloride and 0.5% by weight of o-chlorobenzyl trichloride was obtained from o-chlorotoluene, which had been stored in a steel vessel, and recycled top product (see below) by customary continuous chlorination in an enamelled apparatus. 1 kg of this mixture was blown out discontinously with 10 l of dry nitrogen in an enamelled apparatus at a temperature of 150° C. in the course of 4 hours. Thereafter, the content of amines (+pyridine+nuclearchlorinated pyrimidines) in the mixture was checked and if appropriate brought to a value of 0.02±0.001% by weight by addition of pyridine. The mixture was then distilled continuously in a nickel column (length 4.5 m, internal diameter 70 mm, filled to a height of 4 m with Kerpak ® packing). The bottom temperature was 163° C., the top temperature 138° C., the pressure in the bottom 130 mbar, the pressure at the top 100 mbar and the reflux ratio (reflux to removal at the top) 1.5:1. 0.58 kg per hour of a top product containing 0.8% by weight of o-chlorotoluene, 98% by weight of o-chlorobenzoyl chloride, 1.2% by weight of o-chlorobenzal chloride an small amounts of pyridine an nuclear-chlorinated pyridines was removed and recycled into the chlorination, as well s 0.420 kg per hour of a bottom product containing 0.3% by weight of o-chlorobenzyl chloride, 98.5% by weight of o-chlorobenzal chloride, 1.2% by weight of o-chlorobenzotrichloride and small amounts of pyridine and nuclear-chlorinated pyridines. This distillation was carried out for 100 hours without decompositions being observed.

EXAMPLE 10

The procedures was as in Example 9, but the following mixture was present after the chlorination
1.0% by weight of o-chlorobenzyl chloride,
85.0% by weight of o-chlorobenzal chloride and
14.0% by weight of o-chlorobenzotrichloride.

2.3 kg of this mixture was blown out discontinuously with 23 l of dry nitrogen at 150° C. in the course of 4 hours and the amine content was then adjusted as described in Example 9. During the distillation, the bottom temperature was 165° C., the top temperature 146° C., the pressure in the bottom 130 mbar, the pressure at the top 110 mbar and the reflux ratio 30:1. 0.033 kg per hour of top product containing 60% by weight of o-chlorobenzyl chloride, 40% by weight of o-chlorobenzal chloride and small amounts of pyridine and nuclear-chlorinated pyridines, and 2.297 kg per hour of bottom product containing 0.1% by weight of o-chlorobenzyl chloride, 85.6% by weight of o-chlorobenzal chloride, 14.3% by weight of o-chlorobenzotrichloride and small amounts of pyridine and nuclear-chlorinated pyridines were removed. This distillation was carried out for 100 hours without decompositions being observed.

EXAMPLE 11

The procedure was as in Example 9, but p-chlorotoluene was chlorinated, a mixture of the following composition being present after the chlorination:
0.1% weight of p-chlorotoluene,
33.3% by weight of p-chlorobenzyl chloride,
60.0% by weight of p-chlorobenzal chloride and
6.6% by weight of p-chlorobenzotrichloride.

0.975 kg of this mixture was blown out discontinuously with 10 l of dry nitrogen at 160° C. in the course of 4 hours and the amine content was then adjusted as described in Example 9. During the distillation, the bottom temperature was 167° C., the top temperature 144° C., the pressure in the bottom 130 mbar, the pressure at the top 100 mbar and the reflux ratio 2:1. 0.326 kg per hour of top product containing 0.3% by weight of p-chlorotoluene, 99% by weight of p-chlorobenzyl chloride, 0.7% by weight of p-chlorobenzal chloride and small amounts of pyridine and nuclear-chlorinated pyridines an 0.649 kg per hour of bottom product containing 0.3% by weight of p-chlorobenzyl chloride, 89.7% by weight of p-chlorobenzal chloride, 10% by weight of p-chlorobenzotrichloride and small amounts of pyridine and nuclear-chlorinated pyridines were removed. This distillation was carried out for 100 hours without decompositions being observed.

EXAMPLE 12

The procedure was as in Example 9, but 2,4-dichlorotoluene was chlorinated, a mixture of the following composition being present after the chlorination:
20% by weight of 2,4-dichlorobenzal chloride and
80% by weight of 2,4-dichlorobenzotrichloride.

1.68 kg of this mixture were blown out discontinuously with 17 l of dry nitrogen at 160° C. in the course of 4 hours and the amine content was then adjusted as described in Example 9. During the distillation, the bottom temperature was 198° C., the top temperature 165° C., the pressure in the bottom 198 mbar, the pressure at the top 165 mbar and the reflux ratio 1.5:1. 0.336 kg per hour of top product containing 99.2% by weight of 2,4-dichlorobenzal chloride, 0.8% by weight of 2,4-dichlorobenzotrichloride and small amounts of pyridine and nuclear-chlorinated pyridines and 1.344 kg per hour of bottom product containing 0.2% by weight of 2,4-dichlorobenzal chloride, 99.8% by weight of 2,4-dichlorobenzotrichloride and small amounts of pyridine and nuclear-chlorinated pyridines were removed. This distillation was carried out for 100 hours without decompositions being observed.

EXAMPLE 13 (for comparison)

9 kg of a mixture of 23% by weight of 2,4- and 2,5-dichlorobenzal chloride, 35% by weight of 2,6-dichlorobenzal chloride and 42% by weight of 2,4- and 2,5-dichlorobenzotrichloride which has been prepared analogously to Example 9 from a dichlorotoluene mixture were blown out with 30 l of dry nitrogen at 160° C. in the course of 4 hours. The blown out mixture was distilled in an apparatus as described in Example 9 in the absence of pyridine an nuclear-chlorinated pyridines. After 2 kg had been distilled off at a bottom temperature of 190° C., at top temperature of 170° C., a pressure in the bottom of 100 mbar, a pressure at the top of 70 mbar and a reflux ratio of 3:1, the 7 kg which remained in the sump formed a resinous product which could no longer be distilled.

What is claimed is:
1. A process for the distillation of a mixture containing alkylaromatics chlorinated in the alkyl side chain which comprise a compound of the formula (I)

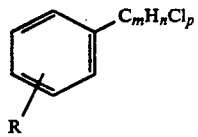 (I)

in which
- m represents an integer from 1 to 4,
- n represents zero or an integer from 1 to 2 m and
- p represents an integer from 1 to 2 m+1,
- wherein n+p always gives 2 m+1, and
- R is selected from the group consisting of 1 to 3 halogen atoms and a nitro group, comprising
  a) stripping the mixture to be distilled by directly contacting the mixture with an inert gas at a temperature between 100° to 200° C., in order to remove gaseous HCl, before the distillation and
  b) distilling the stripped mixture in distillation equipment in the presence of amines and/or chlorinated amines.

2. The process of claim 1, in which the formula (I) R is selected from the group consisting of 1 to 2 chlorine atoms and a nitro group.

3. The process of claim 1, in which the stripping is carried out until a content of non-bonded chlorine of less than 10 ppm ad a content of hydrogen chloride and water of in each case less then 30 ppm are present in the mixture to be distilled.

4. The process of claim 1, in which the amines and/or chlorinated amines are present in all parts of the distillation equipment.

5. The process of claim 1, in which amines and/or chloroamines are present in a total amount of 0.02 to 0.2% by weight, based on the mixture to be distilled.

6. The process of claim 1, in which nitrogen-containing organic heterocyclics and/or nuclear-chlorinated derivatives thereof are present as the amines and/or chlorinated amines.

7. A process according to claim 1, wherein the said temperature is between 120° C. to 180° C.

8. A process according to claim 1, wherein the inert gas is free from steam.

9. A process according to claim 1, wherein the inert gas is free from oxygen.

10. A process for the distillation of a mixture containing alkylaromatics chlorinated in the alkyl side chain in which the mixture is obtained by chlorination of the alkyl side chain with elemental chlorine of a compound of the formula (II)

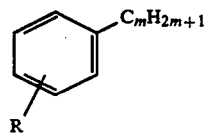 (II)

in which
- m represents an integer from 1 to 4 and
- R is selected from the group consisting of 1 to 3 halogen atoms and a nitro group, comprising
  a) stripping the mixture to be distilled with an inert gas at a temperature between 100° to 200° C., in order to remove gaseous HCl, before the distillation and
  b) distilling the stripped mixture in distillation equipment in the presence of amines and/or chlorinated amines.

11. The process of claim 10, in which the mixture is obtained by the side chain chlorination of chlorotoluenes.

* * * * *

UNITED STATES PATENT AND TRADEMARK OFFICE
CERTIFICATE OF CORRECTION

PATENT NO. : 5,273,627
DATED : December 28, 1993
INVENTOR(S) : Rohlk, Kai

It is certified that error appears in the above-indentified patent and that said Letters Patent is hereby corrected as shown below:

Col. 9, line 29   Delete " ad " and substitute -- and --

Signed and Sealed this

Eleventh Day of February, 1997

Attest:

BRUCE LEHMAN

*Attesting Officer*   *Commissioner of Patents and Trademarks*